(12) United States Patent
Savage et al.

(10) Patent No.: US 6,319,221 B1
(45) Date of Patent: Nov. 20, 2001

(54) SYSTEM FOR FLUID RETENTION MANAGEMENT

(75) Inventors: George M. Savage, Portola Valley; Georgi Lathbury, Fremont; Jeffrey J. Christian, San Jose, all of CA (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/454,878

(22) Filed: Dec. 3, 1999

Related U.S. Application Data

(62) Division of application No. 09/068,059, filed on Dec. 14, 1998, now Pat. No. 6,238,366.

(51) Int. Cl.[7] .................................................. A61M 1/00
(52) U.S. Cl. ....................................................... 604/28
(58) Field of Search .......................... 604/26, 27, 28, 604/29, 246, 247, 248, 249, 4–9, 65–67, 21–25

(56) References Cited

U.S. PATENT DOCUMENTS

| | | |
|---|---|---|
| 3,648,698 | 3/1972 | Doherty . |
| 3,699,815 | 10/1972 | Holbrook . |
| 3,704,709 | 12/1972 | Sorenson et al. . |
| 3,745,999 | 7/1973 | Deaton . |
| 3,845,765 | 11/1974 | Ikeda . |
| 4,060,107 | 11/1977 | Naftulin . |
| 4,190,047 | 2/1980 | Jacobsen et al. . |
| 4,295,537 | 10/1981 | McAvinn et al. . |
| 4,321,922 | 3/1982 | Deaton . |
| 4,346,711 | 8/1982 | Agdanowski et al. . |
| 4,384,580 | 5/1983 | Leviton . |
| 4,388,922 | 6/1983 | Teland . |
| 4,402,687 | 9/1983 | Denty et al. . |
| 4,419,093 | 12/1983 | Deaton . |
| 4,449,538 | 5/1984 | Corbitt et al. . |
| 4,460,361 | 7/1984 | Nichols . |
| 4,516,973 | 5/1985 | Teland . |
| 4,522,623 | 6/1985 | Lauterjung . |
| 4,650,464 | 3/1987 | Ruiz et al. . |
| 4,670,007 | 6/1987 | Wheeldon et al. . |
| 4,675,010 | 6/1987 | Siposs et al. . |
| 4,675,011 | 6/1987 | Kurtz et al. . |
| 4,712,567 | 12/1987 | Gille et al. . |
| 4,775,360 | 10/1988 | Lane et al. . |
| 4,795,448 | 1/1989 | Stacey et al. . |
| 4,798,578 | 1/1989 | Ranford . |
| 4,889,528 | 12/1989 | Nadai et al. . |
| 4,898,593 | 2/1990 | Swisher et al. . |

(List continued on next page.)

FOREIGN PATENT DOCUMENTS

| | | |
|---|---|---|
| 0097432 | 1/1984 | (EP) . |
| 0112104 | 6/1984 | (EP) . |
| 0498382 | 8/1992 | (EP) . |
| 9528198 | 8/1995 | (EP) . |
| 8501879 | 5/1985 | (WO) . |
| 9527520 | 10/1995 | (WO) . |

Primary Examiner—Manuel Mendez
(74) Attorney, Agent, or Firm—Verne E. Kreger, Jr.

(57) ABSTRACT

The present invention provides a fluid retention management system that records and displays fluid retention of a patient based on the weight of fluid entering and exiting the patient's body. Scales or other weighing devices are used to weigh the fluid entering and exiting the body so that the corresponding fluid volume may be calculated. The system automatically detects when a fluid container is being replaced. The fluid deficit of the patient is calculated according to the difference between the fluid volume entering the patient and the fluid volume exiting the patient. An operator is able to enter the specific gravity of the fluid and a fluid deficit alarm threshold. If the fluid deficit exceeds the alarm threshold, audible and visual alarms are generated.

6 Claims, 11 Drawing Sheets

U.S. PATENT DOCUMENTS

| | | |
|---|---|---|
| 4,922,922 | 5/1990 | Pollock et al. . |
| 4,930,997 | 6/1990 | Bennett . |
| 4,994,026 * | 2/1991 | Fecondini .............................. 604/29 |
| 5,009,275 | 4/1991 | Sheehan . |
| 5,112,323 | 5/1992 | Winkler et al. . |
| 5,158,533 | 10/1992 | Strauss et al. . |
| 5,185,007 | 2/1993 | Middaugh et al. . |
| 5,234,419 | 8/1993 | Bruant et al. . |
| 5,437,836 | 8/1995 | Yamada . |
| 5,445,610 | 8/1995 | Evert . |
| 5,470,324 | 11/1995 | Cook et al. . |
| 5,492,537 | 2/1996 | Vancaillie . |
| 5,725,516 | 3/1998 | Cook et al. . |

* cited by examiner

SYSTEM FOR FLUID RETENTION MANAGEMENT

This is a Divisional of prior application No.: 09/068,059, filed Dec. 14, 1998 now U.S. Pat. No. 6,238,366.

BACKGROUND OF THE INVENTION

The present invention is related to medical devices and, more particularly, to medical devices for monitoring fluid retention levels in a patient during a medical procedure.

Fluid management is crucial in many medical procedures. Oftentimes, a patient is exposed to relatively large volumes of saline or other perfusion fluids. In some procedures, fluid is introduced into a patient's body to flush out impurities (e.g., dialysis). In other procedures, fluid is introduced into a patient's body to act as a distending medium. During these procedures, excessive fluid retention by the patient may be dangerous and even fatal.

As an example, electrosurgical procedures such as hysteroscopic endometrial resection and transurethral resection of the prostate require the use of a non-conductive irrigant fluid as a distending medium. Excessive absorption of the irrigant fluid by the patient can be detrimental so it is important for the operating room staff to keep track of how much fluid has been absorbed by the patient.

In order to monitor fluid levels, many irrigant bags are prefilled by the manufacturer or include fluid level markings. The operating room staff may attempt to keep a running estimate of how much fluid has been absorbed by the patient according to the difference between the volume of fluid in and the volume of fluid out. However, in addition to the possible human error, the irrigant bags routinely do not provide an accurate volume measurement as the manufacturer may overfill the irrigant bag or the fluid level markings on the bag are not appropriate for precise measurement. Therefore, this method of measuring patient fluid level retention is inaccurate and results in low physician confidence.

Other known fluid retention management systems are based on measuring the rate of fluid flowing into the patient and the rate of fluid flowing out of the patient. However, small errors in the measured rate can produce large errors in the total fluid retention over time. Therefore, this approach does not provide an accurate measurement of fluid retention of a patient.

During certain endoscopic surgeries, especially therapeutic hysteroscopic or urologic procedures, considerable volumes of irrigation fluid must be infused into and recovered from a patient in order to ensure good visibility and proper distension of the cavity being viewed. Typical endoscopes operate at flow rates of more that 500 ml per minute. Typically, fluid irrigant bags range from 1 to 3 liters and collection canisters are not larger than 3 liters. Therefore, every few minutes, the circulating nurse must change a collection canister which involves becoming contaminated with bloody fluid. The nurse must then rapidly change gloves so that an irrigation bag may be changed.

Under this scenario, the nurse is continuously occupied with fluid management and is required to lift heavy irrigation bags overhead and stoop to change heavy collection canisters. In addition, the nurse has to constantly be aware of the fluid deficit status in order to keep the physician apprised of any excessive (e.g., more than 1.5 liters) fluid absorption by the patient.

SUMMARY OF THE INVENTION

The present invention provides highly accurate methods and systems of measuring fluid retention of a patient.

According to the present invention, the fluid retention or loss of a patient is determined by weighing fluid introduced into the patient to produce a fluid-in amount, weighing fluid collected from the patient to produce a fluid-out amount, and calculating a difference between the fluid-in amount and the fluid-out amount with the difference representing the fluid retention or loss of the patient. Additionally, the fluid amounts may be volumes calculated by dividing the weight of fluid by the specific gravity of the fluid input by an operator.

An embodiment of the present invention provides a method for measuring fluid retention or loss of a patient comprising the steps of: storing fluid in an inflow container such that the inflow container supplies fluid introduced into the patient; weighing fluid in the inflow container to produce a fluid-in amount; storing fluid in an outflow container such that the outflow container receives fluid collected from the patient; weighing fluid in the outflow container to produce a fluid-out amount; automatically detecting if an inflow or outflow container is replaced; and calculating a difference between the fluid-in amount and the fluid-out amount, the difference representing the fluid retention or loss of the patient. The user may be signaled by audio and/or visual signals when a container is removed and the container has been replaced.

Another aspect of the present invention provides a system for fluid management of a patient that reduces the amount of time required to tend to the inflow and outflow containers. The fluid management system comprises an inflow container for storing fluid introduced into the patient; a pump coupled to the inflow container for assisting fluid from the inflow container into the patient; and an outflow container for storing fluid collected from the patient. The pump may pump fluid directly into the patient or into an irrigant bag where the fluid flows into the patient with the force of gravity.

Other features and advantages of the present invention will become readily apparent upon a perusal of the following description and the accompanying drawings.

DETAILED DESCRIPTION OF PREFERRED EMBODIMENTS

The present invention provides highly accurate methods and systems for fluid retention management which utilize the weight of the fluid introduced into the patient and the weight of the fluid collected from the patient to calculate the total fluid retention. Although the embodiment described in the following paragraphs determines the fluid retention of the patient, the present invention may also be utilized to determine the fluid loss. Therefore, the description of the embodiment is illustrative and not limiting.

Figure 1:
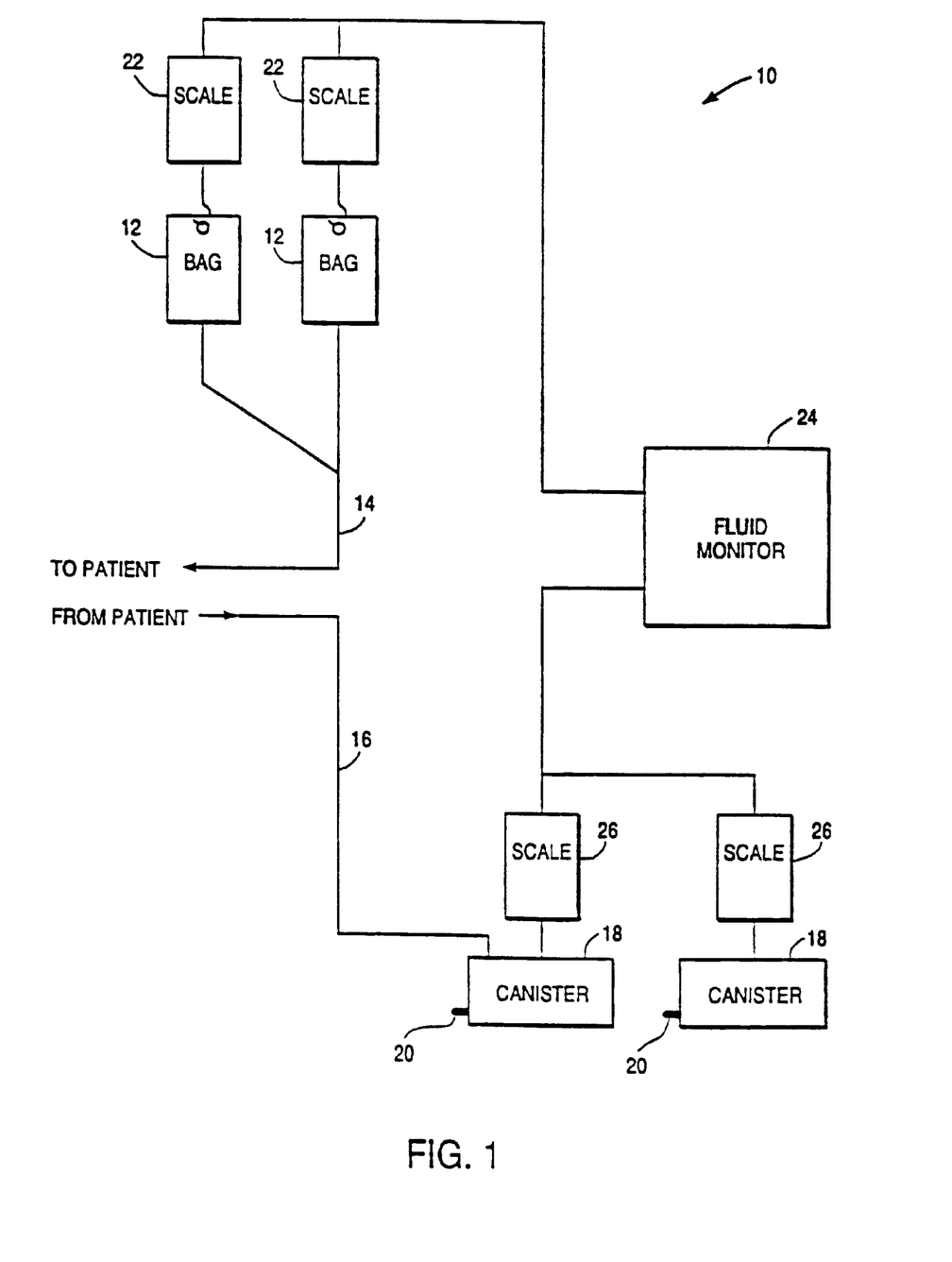
FIG. 1 shows a system of fluid retention management according to the present invention.

FIG. 1 shows a fluid retention management system according to the present invention. A fluid retention management system 10 includes irrigant bags 12 which retain the irrigant fluid before it is introduced into a patient's body. The irrigant fluid flows into the patient from the irrigant bags through a tube 14. As shown, the irrigant bags are typically suspended higher than the patient so that the force of gravity will aid irrigant fluid flow into the patient. Although two irrigant bags are shown, any number of irrigant bags may be utilized with the present invention.

The irrigant fluid flows out of the patient through a tube 16 and enters collection canisters 18. As shown, the collection canisters may be suspended lower than the patient so that the force of gravity draws the irrigant fluid into the canisters. Additionally, canisters 18 include fittings 20 which allow a suction device (not shown) to be attached to the canisters to increase fluid flowing out of the patient. The canisters may be connected in series and/or parallel to provide a large effective collection volume. Although two canisters are shown, any number of canisters may be utilized with the present invention.

In the description that follows, it will be assumed that irrigant fluid that leaves the irrigant bags enter the patient's body. Thus, the amount of irrigant fluid introduced into the patient's body is calculated from the change in weight of the irrigant bags. Similarly, it will be assumed that irrigant fluid flowing out of the patient enters the collection canisters and therefore, the amount of irrigant fluid collected from the patient is utilized to calculate the fluid retention of the patient. In general, these assumptions are true; however, there may be instances where some irrigant fluid is spilled so it may be advisable for the physician to interpret the readings of the fluid monitor and make any needed corrections.

The irrigant bags are suspended from scales 22 which weigh the corresponding irrigant bags. Typically, the scales are suspended from an IV pole (not shown). Scales 22 are electrically connected to a fluid monitor 24 which measures the changes in weight of the corresponding irrigant bags from the weight indicated by the scales.

Collection canisters 18 are suspended from scales 26 which weigh the corresponding canisters. Scales 26 are electrically connected to fluid monitor 24 which measures the changes in weight of the corresponding collection canisters from the weight indicated by the scales. As is described in more detail below, the fluid monitor utilizes the changes in weights of the irrigant bags and collection canisters to determine the fluid retention of the patient. The fluid monitor displays the fluid-in amount, fluid-out amount, and fluid deficit (reflecting fluid retention) on a display and warns an operator if the fluid deficit crosses a threshold.

Figure 2:
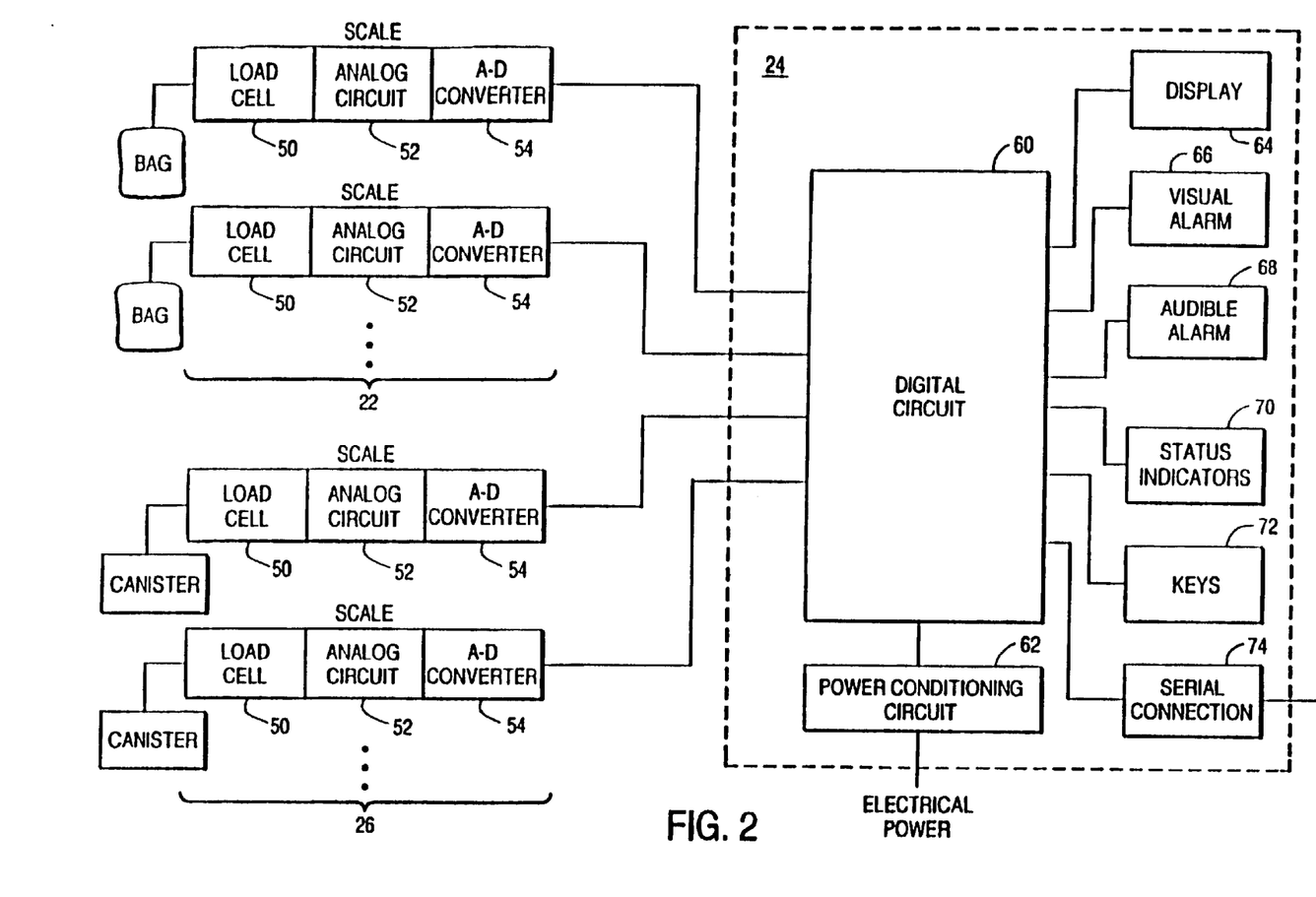
FIG. 2 is a block diagram of a fluid management device.

FIG. 2 shows a block diagram of the fluid retention management device. Each scale 22 and 26 includes a load cell 50, analog circuit 52 and analog-to-digital (A-D) converter 54. A scale is a device that measures the weight of an object. As shown, the scales of a preferred embodiment include load cell 50 which is a mechanical weight sensor. The load cells continuously weigh the irrigant bags and collection canisters to produce varying electrical resistances. The varying electrical resistance from each load cell vary according to changes in weight of the irrigant bag or collection canister, respectively.

Analog circuit 52 receives the varying electrical resistance and performs signal processing to produce an analog electrical signal which is converted to a digital electrical signal by A-D converter 54. The digital signals or counts from the scales represents the weight of the corresponding bag/canister and any associated fluid therein. These digital signals are input to fluid monitor 24.

In one embodiment, analog circuit 52 includes an extremely high input impedance (low drift, low noise) differential instrumentation amplifier with precision for gain adjustment and an inverting voltage follower with offset adjustment (scale zeroing). The analog voltage is adjusted to fall within ±2 volts corresponding to weight on the load cell from 0 to 10,000 grams. A-D converter 54 is a dual-slope integrating A-D converter that subsequently transforms the analog voltage into a digital count between −20,000 and +20,000 with one count corresponding to 0.25 grams with less than ±1 count of noise. The output of the A-D converter is a binary coded decimal count ranging from 0 to 20,000 and a sign bit which are then input to digital circuit 60 of the fluid monitor.

The digital circuit subsequently adds +20,000 to the binary coded decimal count from the A-D converter producing a 16 bit digital integer between 0 and 40,000. This number is then rounded to the nearest 4 counts and divided by 4 resulting in a very stable digital value corresponding to grams. This gram-precision value is used for certain decisions by the digital circuit before it is rounded to the nearest 10 cubic centimeters or ccs for display and logging.

In a preferred embodiment, the A-D converter generates a pulse width and a sign that correspond to the measured weight (e.g., Harris ICL7135). The A-D converter generates a pulse width that is measured utilizing a 300 KHz clock in the fluid monitor. The pulse width is converted to counts (indicative of the duration of the pulse width), where each count is equal to 0.5 grams. The counts are then converted to a binary integer between 1000 and 40,000. All calculations are maintained at their full 0.5 gram resolution until displayed. It is anticipated that the total weight indicated by the A-D converted will be 11,000 grams or more.

The fluid monitor weighs the fluid introduced into the patient by determining the change in weight of the irrigant bags. This change in weight is used to produce a fluid-in amount representing the fluid introduced into the patient. Likewise, the fluid monitor weighs the fluid collected from the patient by determining the change in weight of the collection canisters. This change in weight is used to produce a fluid-out amount representing the fluid collected from the patient. In a preferred embodiment, the fluid-in and fluid-out amounts are volumes but they may alternatively be other quantities including weight.

Fluid monitor 24 includes a digital circuit 60. The digital circuit controls the operation of the fluid monitor and receives power through a power conditioning circuit 62. The fluid monitor displays the fluid-in, fluid-out and fluid deficit amounts on a display 64. If the fluid monitor determines that the fluid deficit has crossed a threshold or is otherwise serious, the fluid monitor activates a visual alarm 66 and an audible alarm 68. The fluid monitor also maintains status indicators 70 that indicate the status of the device and receives input from a user through keys 72. In order to communicate with a computer (e.g., uploading data), the fluid monitor includes a serial connection 74.

Figure 3A:
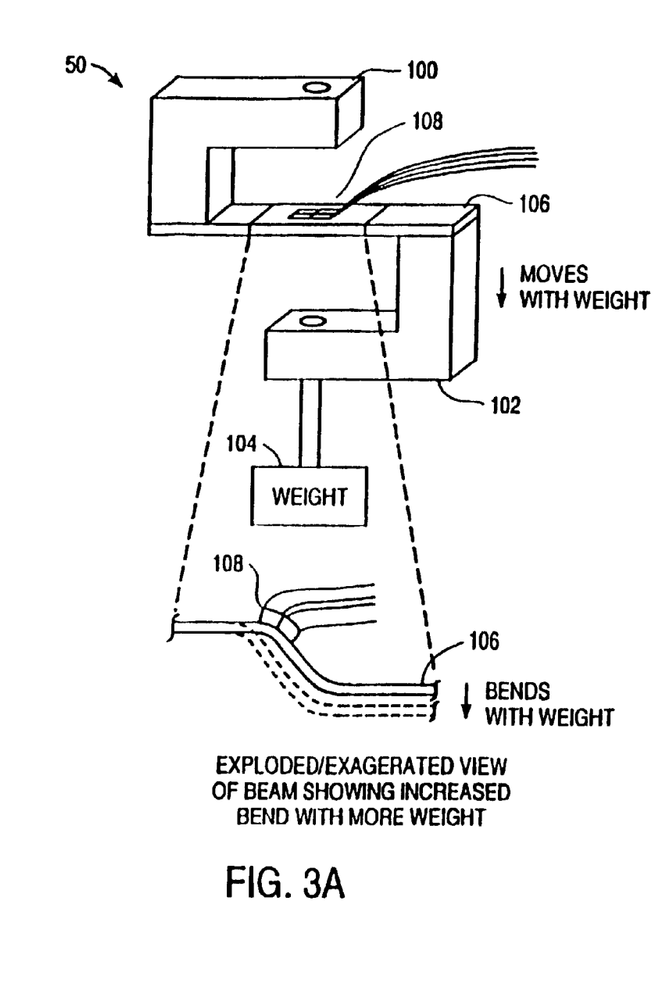
FIG. 3A shows a load cell and FIG. 3B shows a strain gage bridge, both of which may be utilized in a scale.

FIG. 3A shows a load cell that may be utilized in a scale of the present invention. Load cell 50 includes a fixed end 100 and a weighted end 102. The fixed end is secured to a stationary support whereas the weighted end supports a weight 104. The weight may be an irrigant bag or collection canister.

Joining the fixed and weighted ends is a bendable beam 106. The bendable beam bends in response to the weight attached to weighted end 102. A strain gage 108 is attached to the bendable beam. The strain gage is a small piezo-resistive element that changes resistance proportionally to the bending of bendable beam 106. As the bendable beam bends in response to weight 104, the strain gage changes resistance according to the weight supported by the load cell.

Figure 3B:
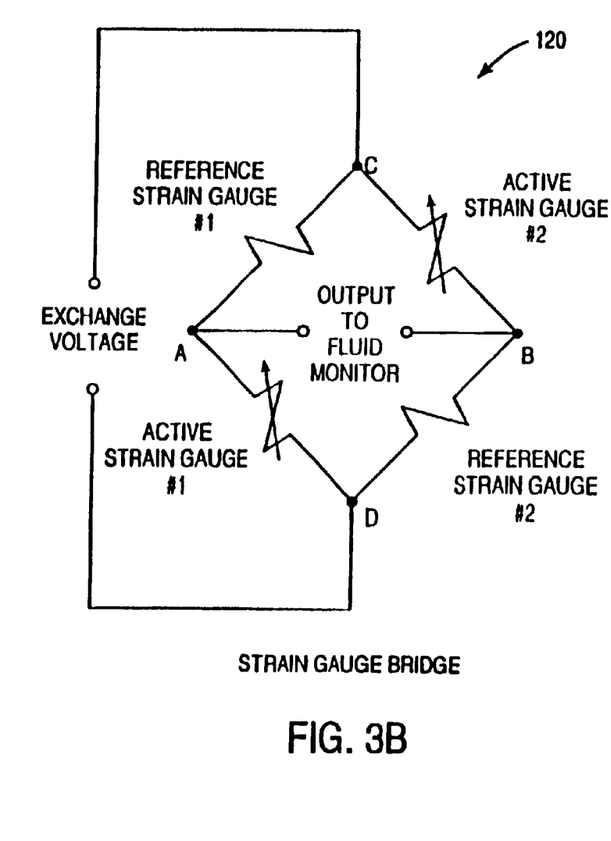

FIG. 3B shows a strain gage bridge for use in a scale. In a preferred embodiment, four strain gages are configured into a strain gage bridge. A strain gage bridge 120 is a Wheatstone bridge with two reference strain gages and two active strain gages. The reference strain gages do not change resistance with bending of the bendable beam, but act to compensate for temperature changes which also affect resistance in the piezo-resistive element. Although the active strain gages change resistance with bending of the bendable beam, the resistance changes of the active strain gages are in opposite directions (i.e., when resistance is increasing in one, it is decreasing in the other, and vice versa).

An excitation voltage of approximately 10 volts DC is applied to strain gage bridge 120 at points C and D. A resulting voltage between points A and B is proportional to change in resistance of the active strain gages. This resulting voltage is applied to a high input impedance analog amplifier and ultimately is converted to a digital count proportional to weight on the load cell.

Figure 3C:
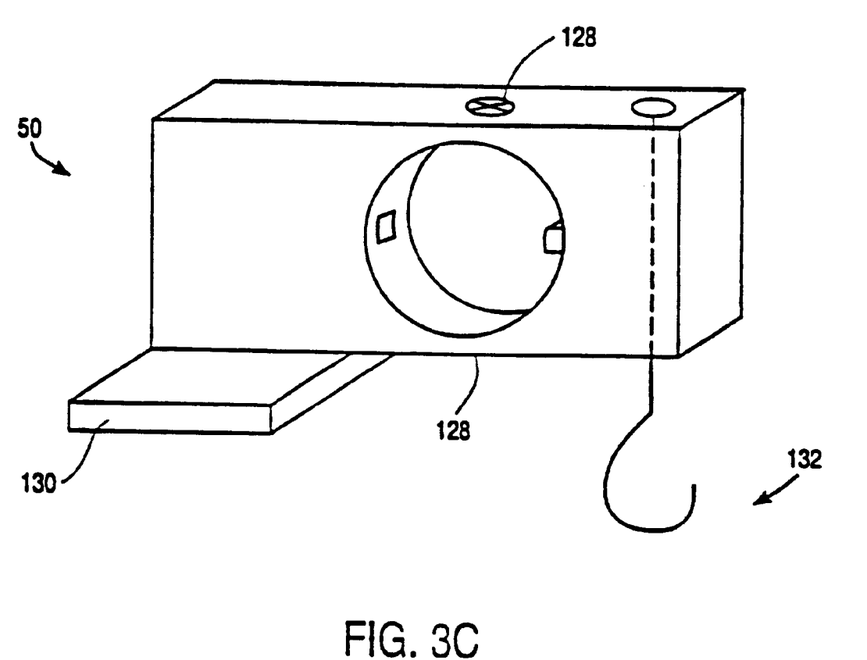
FIG. 3C shows a dual bending beam load cell.

FIG. 3C shows a dual bending beam load cell of utilized with a preferred embodiment of the invention. Load cell 50 is an aluminum block that includes two strain gages 128 located at bending bean sections of the load cell. The load call may be rigidly mounted utilizing a base 130 so that when an irrigant bag or collection canister is placed on a hook 132, the dual bendable beams bend in response to the weight which is detected by the strain gages.

Figure 4:
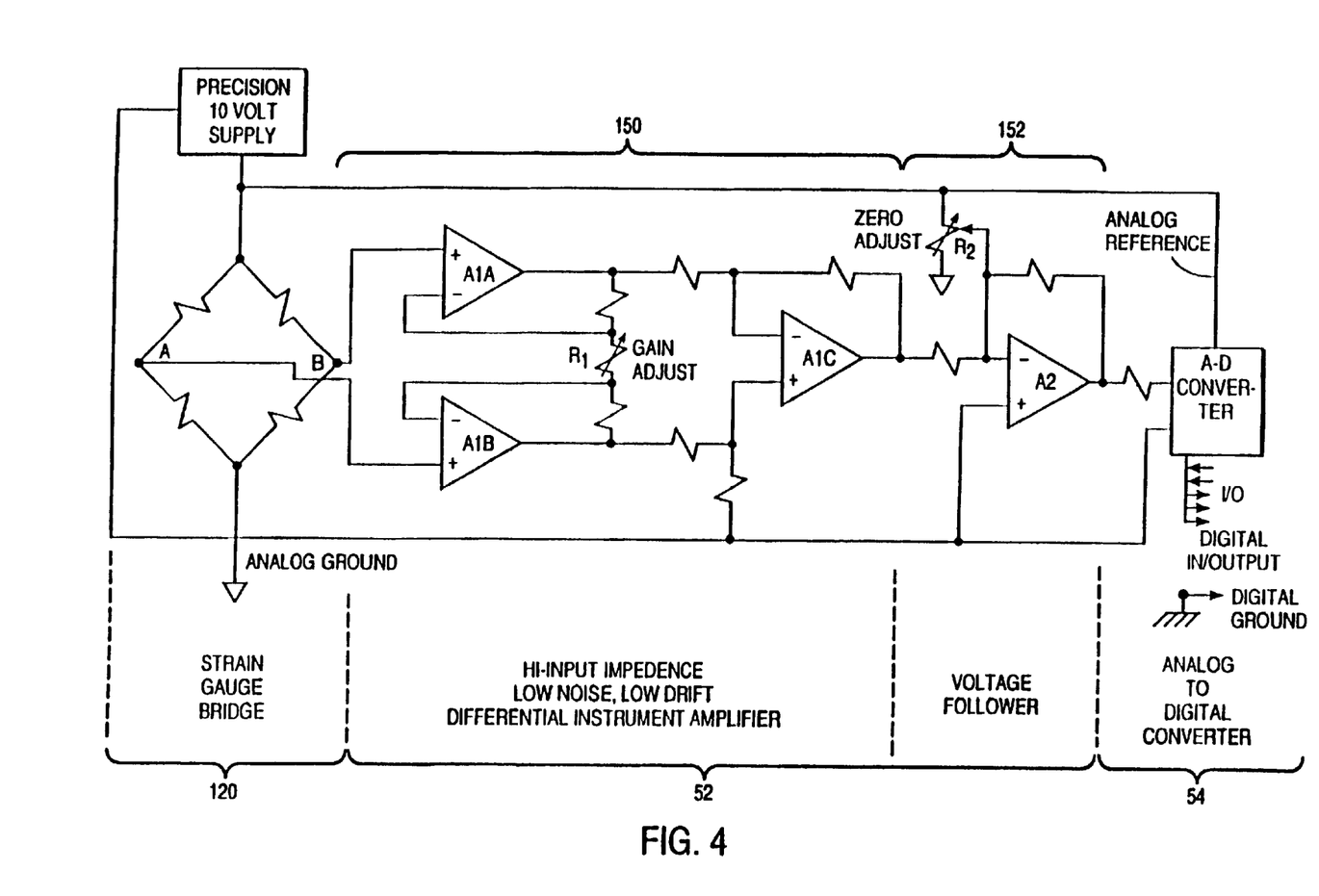
FIG. 4 shows circuity of a scale.

FIG. 4 shows circuitry of a scale including strain gage bridge 120, analog circuit 52 and A-D converter 54. The analog circuit includes a high input impedance low noise, low drift differential instrument amplifier 150 and an inverting voltage follower 152. The instrument amplifier is constructed from 3 operational amplifiers A1A, A1B and A1C. Amplifiers A1A and A1B are high input impedance, extremely low drift chopper stabilized integrated operational amplifiers. When they are configured as in FIG. 4, they exhibit over 1 gigaohm differential input impedance at their noninverting (+) inputs. This is beneficial in limiting the loading on the strain gage bridge so that its sensitivity and linearity are maintained. The gain for the analog circuit is adjusted via Ri and is approximately 100. Operational amplifier A1C converts the differential signal to a single ended signal with respect to analog ground which is fed to amplifier A2.

Voltage follower 152 includes operational amplifier A2 which is a unit gain inverting voltage follower permitting the zero or bias of the analog circuit to be adjusted non-interactively. The output of operational amplifier A2 ranges from −2V to +2V with −2V corresponding to no (or zero) weight on the load cell and is fed directly to A-D converter 54. The precision, low drift, 10 volt supply is used to regulate the strain gage bridge excitation voltage, zero adjustment voltage and the reference voltage for the A-D converter. In this manner, changes in the 10 volt power supply are compensated.

A-D converter 54 is a dual-slope integrating A-D converter. The A-D converter generates 10,000 digital counts per volt of analog input. Thus, 0 to 10,000 grams (approximately 0 to 10,000 ccs of water) will generate −20,000 to +20,000 counts of output when the gain and zero adjustments are set correctly. The A-D converter first integrates the analog signal over a fixed period of time. In one embodiment, the time period is 1/30 of a second so that the 60 Hz power line noise is averaged out. The A-D converter then integrates the reference voltage while counting at 300 KHz until the integrated reference voltage equals the integrated analog signal at which time the final count becomes available for output. A sign bit is also output so an effective 40,000 count output range is available.

In this embodiment, one count corresponds to 0.25 grams. The counting clock and control signals are sent to the A-D converter from digital circuit 60. The output count is sent to the digital circuit as a sequence of binary coded decimal digits. Preferably, the high input impedance of the differential amplifiers is maintained and analog and digital grounds are isolated. Additionally, all passive components are preferably high precision with low temperature coefficients. In a preferred embodiment, one count corresponds to 0.5 grams and this resolution is maintained until displayed.

Figure 5:
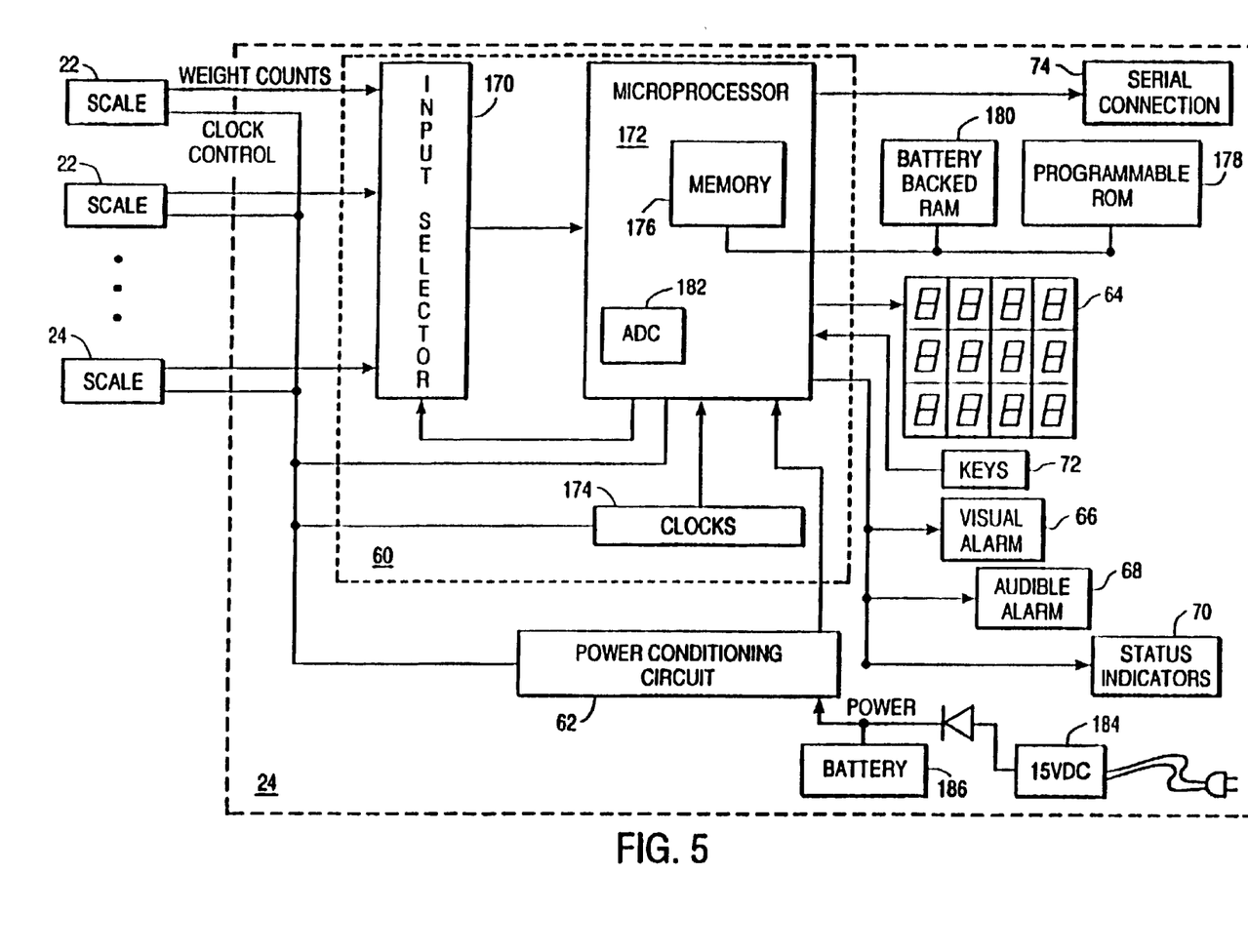
FIG. 5 shows the inputs and outputs of the fluid management device.

FIG. 5 shows the inputs and outputs of the fluid management device. Scales 22 and 26 receive clock and control signals from fluid monitor 24. The scales provide weight counts to an input selector 170 of digital circuit 60. The digital circuit utilizes the input selector to read the digital weight counts from the scales one at a time. The digital circuit also includes a microprocessor 172 and clocks 174. Microprocessor 172 includes memory 176 for storing the program and associated data for the microprocessor during operation. The operating program of the fluid monitor is stored in programmable read-only memory (PROM) 178 which runs upon power-up. Logged data and specific gravities are stored in battery backed random-access memory (RAM) 180.

An A-D converter 182 is integrated with the microprocessor to periodically check certain circuit and battery voltages as part of continuous diagnostics. The microprocessor includes controllers to interface with display 64, visual alarm 66, audible alarm 68, status indicators 70, keys 72, and serial connection 74.

The fluid monitor may powered from an isolated 15 volt DC power supply 184. A large internal lead-acid battery 186 is used during external power failures. The power from power supply 184 or battery 186 is conditioned by power conditioning circuit 62. In a preferred embodiment, the system is powered by a +15, −15 and +5 volt modular supply which does not require the use of a lead-acid battery.

Figure 6:
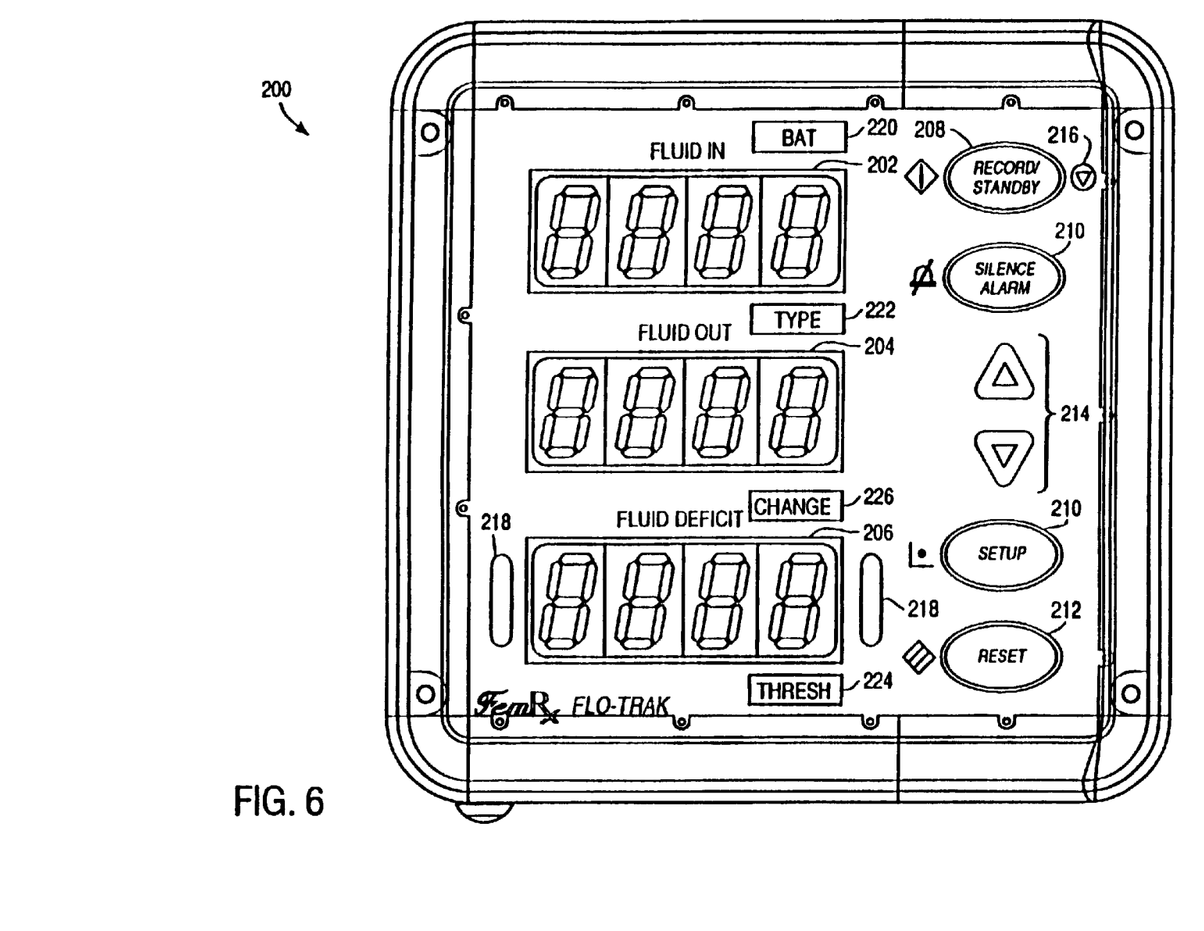
FIG. 6 shows the display panel associated with the fluid monitor.

FIG. 6 shows the display panel of the fluid monitor. Display panel 200 includes a fluid-in readout 202, a fluid-out readout 204, and a fluid deficit readout 206 (all three being display 64). The fluid monitor continuously monitors the weight of fluid flowing into and out of a patient. The fluid monitor converts the weights into the volume of fluid utilizing the fluid's specific gravity. The fluid-in volume is displayed on readout 202 and the fluid-out volume is displayed on readout 204. The fluid monitor calculates the fluid deficit by subtracting the fluid-out volume from the fluid-in volume so that the fluid deficit volume is equal to the fluid retention of the patient. In a preferred embodiment, the fluid volumes are displayed in units liters with a precision of 0.01 liter (or 10 ccs).

Display panel 200 also includes keys for user input. The display includes a RECORD/STANDBY key 208, a SILENCE ALARM key 210, a SETUP key 210, and a RESET key 212. Additionally, the display panel includes up and down arrow keys 214. The display panel has a standby light 216 and alarm lights 218. The display panel has a battery power light 220 that illuminates when the battery is low, a fluid type select light 222 that illuminates when the user is inputting the fluid type of the irrigation fluid and a alarm threshold set light 224 that illuminates when the user is inputting the fluid deficit alarm threshold. The lights are typically LEDs.

In a preferred embodiment, the display panel has a change light 226. The change lights indicate when one of the scales is unstable or in the process of establishing stability during a fluid container change. The change lights may be accompanied by an audible sound. Thus, for example, when an operator removes a collection canister to empty the fluid, fluid monitor detects that the weight of the collection canister has quickly gone to zero (or that the weight is unstable as a result of being removed). The fluid monitor issues visual and audible signals to the operator to indicate that an unstable condition has been detected. Once the operator replaces the empty collection canister on the scale, the fluid monitor detects a stable condition and issues visual and audible signals to the operator to indicate a stable condition has been detected and that the fluid container change is complete. The fluid monitor also resets the baseline weight of the replaced fluid container.

By automatically detecting when a fluid container is replaced (e.g., with a full container or an empty container), the present invention allows an operator great freedom in monitoring the fluid loss or retention of the patient. The operator is not required to remember a complicated procedure for replacing a fluid container. Instead, the operator changes the fluid container and the fluid monitor automatically detects the change and resets the baseline weight without requiring operator input.

Figure 7:
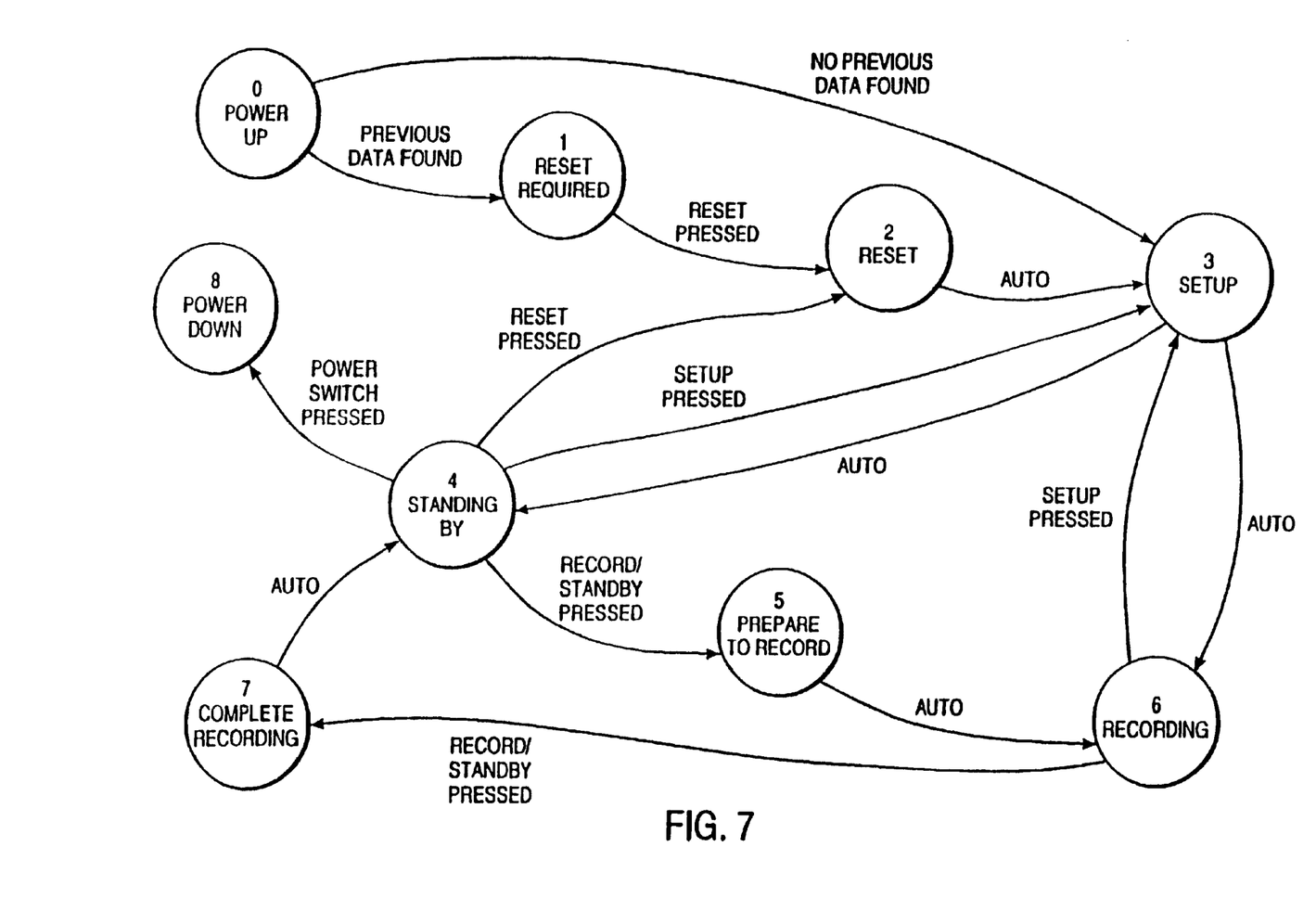
FIG. 7 is a state diagram of the software of the fluid monitor.

FIG. 7 is a state diagram of the software that directs the operation of the fluid monitor. In general, the fluid monitor is in one of two modes: record mode and standby mode. In record mode, fluid is flowing and measurements are being taken, recorded and logged. In standby mode, no fluid is flowing, logging has stopped and the display reflects the current values for the data. Recorded data can also be uploaded in standby mode. In a preferred embodiment, the running software program is in one and only one mode (record mode or standby mode) at any instant in time.

The software program of the present invention is event and state driven which means the fluid monitor will respond to events and the action taken in response to those events will be determined by the current state of the system. Once the power is turned on, the program enters standby mode and the fluid monitor is in state 0. In state 0 the system performs initialization including reading configuration data from memory. The configuration data may include a system ID, number of possible fluid types and specific gravity for each type of fluid. During initialization, the system determines if previous data has been logged into memory. If the previous logged data is still present, values for the fluid type, the fluid deficit alarm threshold, and values for the fluid-in, fluid-out and fluid deficit are read in from memory. The values are displayed on the display as appropriate and standby light 116 flashes to indicate previous data is present. If previous data is found, the system proceeds to state 1. Otherwise, if no previous data is found, the system proceeds to state 3.

In state 1, the system retains previous data and a reset is required. In order to reset the system the user depresses the RESET key for more than two seconds and the system proceeds to state 2. The user may also initiate uploading of previous data while in state 1 by connecting a cable from a suitable computer and running a utility program in the computer. This is done prior to pressing the RESET key.

Once the user has initiated a reset of the system, the system clears the log of previous data including the baseline weights and current weights for the fluids at state 2. The baseline weights are the initial weights of the irrigant bags or collection canisters. Thus, the baseline weights are typically the weight of the full irrigant bags and empty collection canisters. Upon reset, the most recently selected values for the fluid type, and associated specific gravity, and fluid deficit alarm threshold are not cleared but are retained. After resetting, the system proceeds to state 3.

The system may arrive in state 3 from a number of other states. If the system proceeded to state 3 from state 0, state 2 or state 4, the system is in standby mode. In standby mode, the operator is able to select the fluid type and the fluid deficit alarm threshold. Initially, the operator selects the fluid type utilizing up and down arrows 114 to select a number which corresponds to a specific fluid. As the system is in standby mode, the readouts on the display are clear except for fluid-out readout 102 which displays the number of the currently selected fluid type. In a preferred embodiment, the fluids and their associated fluid type selection numbers are printed on the back of the fluid monitor.

After the fluid type is selected in the standby mode, the operator presses the SETUP key and enters the fluid deficit alarm threshold. The currently selected fluid deficit alarm threshold is displayed in fluid deficit readout 104 and the operator is able to increase or decrease the alarm threshold utilizing up and down arrows 114. The fluid deficit alarm threshold is in units of 0.01 liters and establishes the value of the difference between the fluid-in amount and fluid-out amount, above which the alarm will activate. Once the fluid deficit alarm threshold is selected, the operator presses the SETUP key and the system proceeds to state 4.

If the system arrives in state 3 in recording mode from state 6, the operator is only able to select the fluid deficit alarm threshold. The current fluid deficit alarm threshold is displayed in fluid deficit readout 104. The operator adjusts the alarm threshold utilizing up and down arrows 114. Once the new fluid deficit alarm threshold is selected, the operator presses the SETUP key and the system returns to state 6.

In state 4, the system is standing by and only background monitoring takes place. Background monitoring may include checking the battery to insure that sufficient power is available. In this state, the system proceeds to state 2 if the operator presses the RESET key for more than two seconds. If the operator presses the SETUP key, the system proceeds to state 3. The operator may also power down the fluid monitor by depressing the power switch on the fluid monitor (not shown).

If the system is in state 4 and the operator presses the RECORD/STANDBY key, the system proceeds to state 5 where the system prepares to record and display data. The system captures all the current weights of the irrigant bags and collection canisters. If the system has yet to record any data then these weights will be used as baseline starting values. Also, if this is the start of a new procedure, the system begins logging data including the system ID, the fluid type and the fluid deficit alarm threshold. Otherwise, if the system is in the middle of recording data, the current weights are used to calculate the fluid-in volume, the fluid-out volume and the fluid deficit volume. The system then proceeds to state 6 and records data.

The user may also initiate uploading of previous data while in state 4 by connecting a cable from a suitable computer and running a utility program in the computer. This is done prior to pressing the RECORD/STANDBY key.

In state 6, the system is event driven and will respond to events including a timer and key input. Thus, the system is in record mode. The operation of the system during a timer event will be described in more detail in reference to FIG. 8. If the SETUP key is pressed during recording, the system proceeds to state 3 and if the RECORD/STANDBY key is pressed, the system proceeds to state 7. An audible and visual alarm is activated if the system detects that the fluid deficit volume has exceeded the alarm threshold. The visual alarm includes flashing alarm lights 118. If the operator presses the SILENCE ALARM key, the system will turn off the audible alarm for two minutes. But after that time the audible alarm will sound again if the alarm condition still exists. The visual alarms are not affected by the SILENCE ALARM key.

In state 7, the system completes recording and saves data to the log. The system remains in record mode. If an alarm condition currently exists, the system continues to convey the alarm warnings. The system then proceeds to state 4 and enters standby mode.

Figure 8:
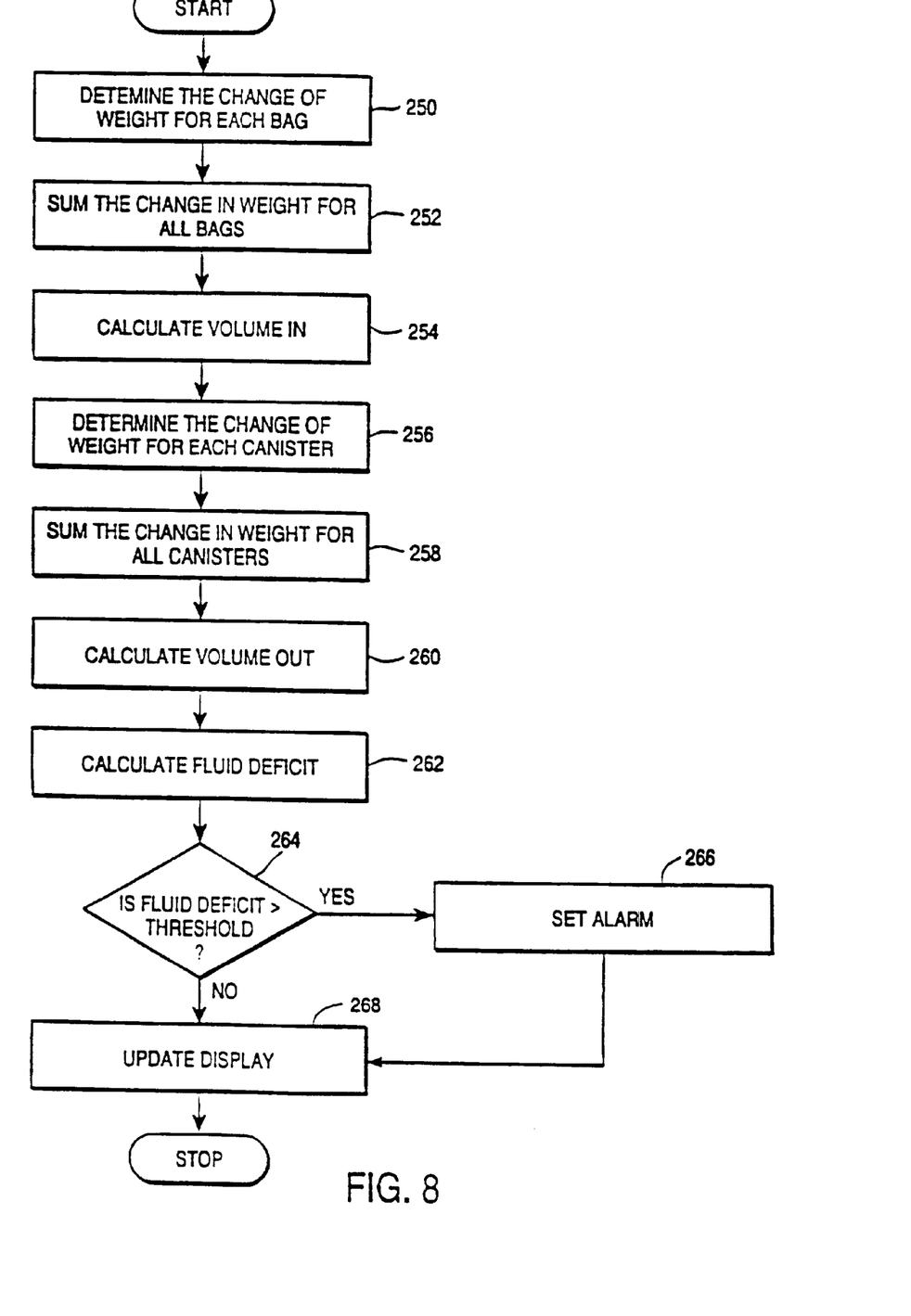
FIG. 8 is a high level flowchart of the process of determining the fluid deficit of the patient.

FIG. 8 is a high level flowchart of the process of determining the fluid level deficit. Although the timer may expire more often than every second, in a preferred embodiment the system records and displays data once each second. However, in other embodiments the rate at which the data is sampled and/or displayed may vary.

At step 250, the system determines the change of weight for each irrigant bag. The current weight for each bag is determined by scales 22. The system determines the change of weight by calculating the difference between the baseline weight and the current weight of each irrigant bag where the baseline weight is the weight of the irrigant bag before fluid flowed from the bag into the patient. The system then sums the change in weights for all of the irrigant bags at step 252. The total change in weight of the irrigant bags is assumed to be equivalent to the weight of fluid entering the patient.

Once the system determines the total change in weight (i.e., fluid-in weight) for all the irrigant bags, the system calculates at step 254 the fluid-in volume by dividing the total weight by the specific gravity of the fluid which has been selected by the operator. When an irrigant bag is empty, an operator may press a "bag change" button which informs the fluid monitor that a new bag will be added and thus a new baseline weight should be calculated. In a preferred embodiment, the system automatically detects when an irrigant bag is changed. The bag's current weight first typically goes to zero as the bag is removed and then increases as a new bag is placed on the scale.

When the system automatically detects the changing of an irrigant bad, the system may signal the user with visual and/or audible cues that the fluid monitor has detected that a bag has first been removed and then replaced. Once an irrigant bag has been replaced, the system then calculates a new baseline weight for the new irrigant bag.

At step 256, the system determines the change of weight for each collection canister. The current weight for each canister is determined by scales 26. The system determines the change of weight by calculating the difference between the baseline weight and the current weight of each canister where the baseline weight is the weight of the canister before fluid flowed out from the patient. The system then sums the change in weights for all of the canisters at step 258. The total change in weight of the canisters is equivalent to the weight of fluid exiting the patient. Once the system determines the total change in weight (i.e., fluid-out weight) for all the canisters, the system calculates at step 160 the fluid-out volume by dividing the total weight by the specific gravity of the fluid which has been selected by the operator.

In a preferred embodiment, the system automatically detects when a collection canister is replaced as discussed above. Once the system detects that a collection canister has been replaced, the system calculates a new baseline weight for the new canister. Although the system may automatically detect the replacement (including refilling or emptying) of both irrigant bags and collection canisters, the system may also only detect the replacement of one type of fluid container depending on the specific embodiment.

Although the system is described as utilizing the same specific gravity for the fluid introduced into and collected from the patient, in other embodiments, a different specific gravity may be entered if these values differ. Thus, the present invention is not limited to a single specific gravity.

The system then calculates the total fluid deficit at step 262. The total fluid deficit is calculated by subtracting the fluid-out volume from the fluid-in volume. Thus, the fluid deficit represents the fluid retention of the patient. In a preferred embodiment the fluid deficit is set to zero if the result is a negative value (meaning fluid loss).

At step 164 the system determines if the fluid deficit is greater than the fluid deficit alarm threshold. If the fluid deficit is greater than or equal to the alarm threshold, the system sets the audible and visual alarms to alert the operator that a fluid retention condition exists. The system then displays the fluid-in volume, fluid-out volume and fluid deficit on the appropriate readouts of display panel 200.

Data that has been logged into memory may be uploaded to a personal computer through a serial connection 74. After the data is uploaded to the personal computer, a flag is set in system memory of the fluid monitor to show that the log has been uploaded since the last recording. Data is retained in the fluid monitor until cleared by a system reset utilizing the RESET key.

The present invention also provides a system for fluid management of a patient that reduces the amount of time required to tend to the irrigation bags and collection canisters. The continuous need to lift heavy irrigant bags and change heavy collection canisters is reduced or eliminated. This gives the operator more time to pay attention to the patient's fluid status. In a preferred embodiment, the system utilizes the fluid monitor described above which continuously displays the fluid-in amount, fluid-out amount and fluid deficit calculated from the weight of the respective fluids.

Figure 9:
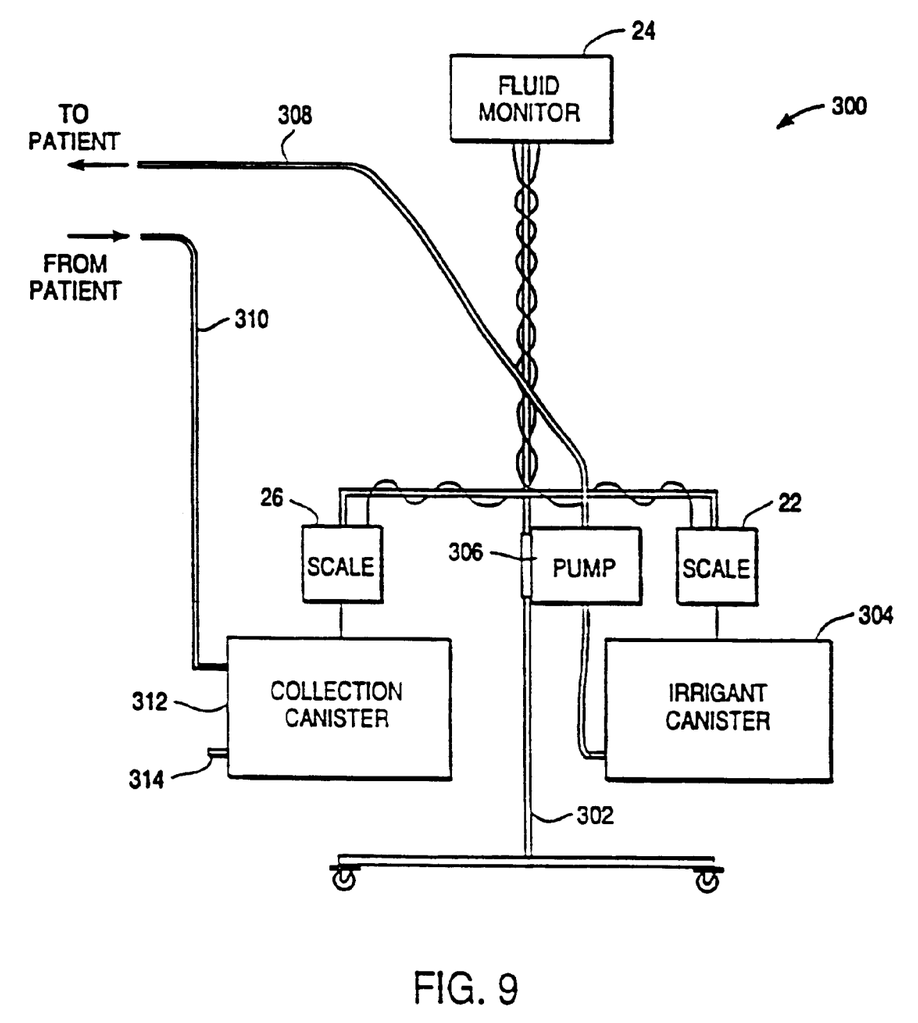
FIG. 9 shows another system of fluid retention management.

FIG. 9 shows a system of fluid retention management that reduces the frequency with which the inflow and outflow containers must be changed. A fluid retention management system 300 includes a stand 302 which supports fluid monitor 24 and scales 22 and 26. The stand may also be a waist high equipment cart. An irrigant canister 304 is suspended from scale 22. The irrigant canister retains the irrigant fluid before it is introduced into the patient's body. As shown, the irrigant canister may be large (e.g., 20 liters) so that the irrigant canister does not have to be changed or refilled often.

A delivery pump 306 pumps the irrigant fluid from the irrigant canister directly into the patient. The pump preferably has appropriate flow capability and safety features to prevent unsafe pressure (e.g., intra-uterine pressure). In one embodiment, the pump is a centrifugal pump with maximum capability of 110 mm Hg and back-up alarm sensor. This allows an operator to set the desired delivery pressure and be notified if the delivery pressure reaches an undesirable level.

The irrigant fluid flows from pump 306 into the patient through a tube 308. The irrigant fluid flows out of the patient through a tube 310 and enters a collection canister 312. The collection canister is suspended from scale 26 and is preferably large so that the collection canister does not have to be changed or emptied often. The collection canister may also have a fitting 314 which allow a suction device (not shown) to be attached to increase fluid flow out of the patient.

In one embodiment, the collection canister is a large collapsible vacuum canister (e.g., 20 liters). Disposable containers fit inside a rigid shell to which vacuum is applied. The rigid shell may also contain graduations visible from the outside to allow the operator to visually estimate the amount of fluid recovered.

If the collection canister or canisters provide a high enough volume of collection fluid, high-volume procedures may be completed without requiring the operator to change a collection canister, thereby contaminating the operator's hands with bloody fluid. Thus, although one large irrigant canister and one large collection canister are shown, the fluid volume may also be increased by increasing the number of canisters. In one embodiment, the irrigant and collection canisters are sized and numbered so that the canisters will not have to be attended to during an operation.

Figure 10:
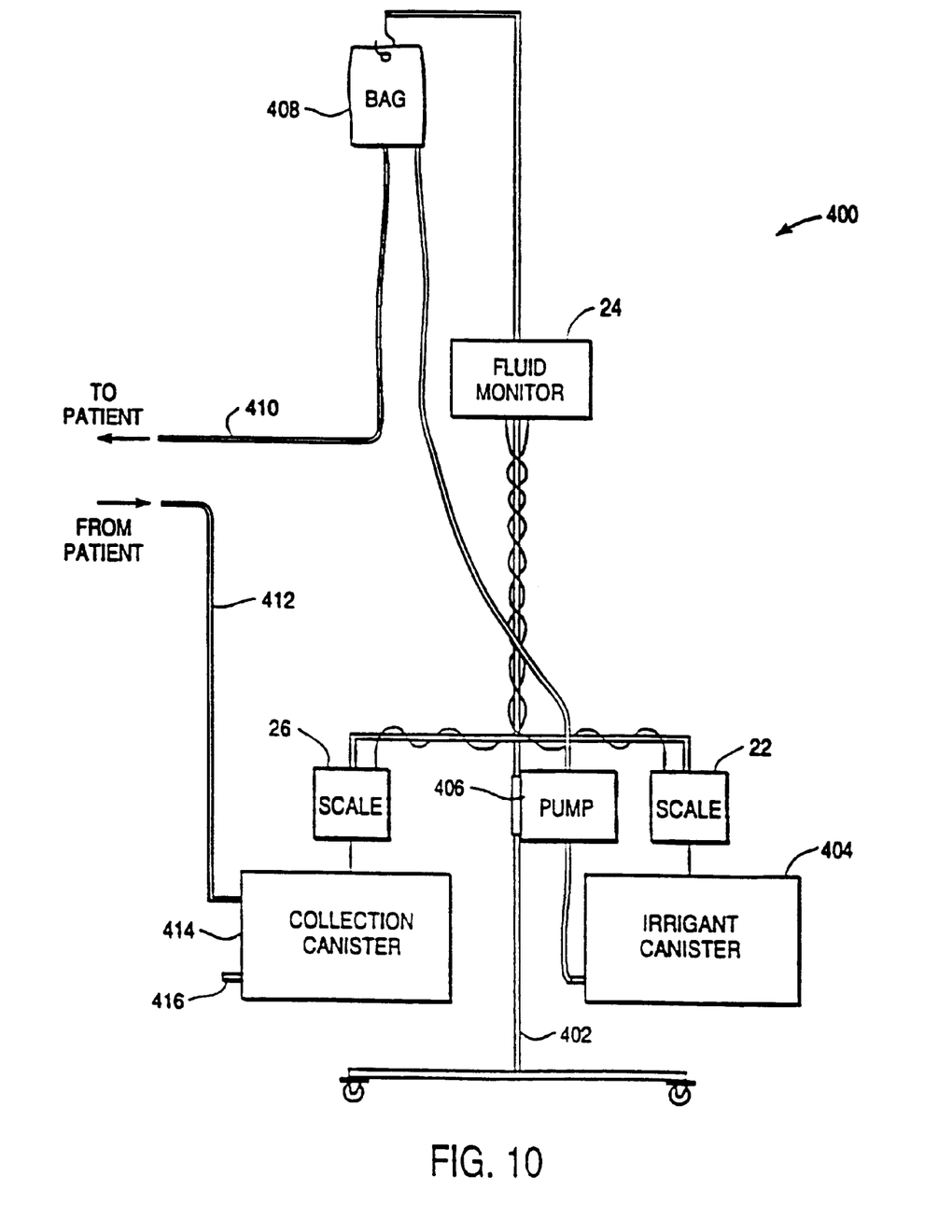
FIG. 10 shows another system of fluid retention management.

FIG. 10 shows another system of fluid retention management that reduces the frequency with which the inflow and outflow containers must be changed. A fluid retention management system 400 includes an IV pole 402 which supports fluid monitor 24 and scales 22 and 26. An irrigant canister 404 is suspended from scale 22. The irrigant canister retains the irrigant fluid before it is introduced into the patient's body. As shown, the irrigant canister may be large (e.g., 20 liters) so that the irrigant canister does not have to be changed or refilled often.

A delivery pump 406 pumps the irrigant fluid from the irrigant canister into an irrigant bag 408. The pump may be a centrifugal pump with a modest (and predetermined) pressure capability, together with a carefully calibrated check valve, to keep relatively small irrigant bag 408 (e.g., 250 cc) on the IV pole filled with a constant volume of fluid. Irrigant fluid flows out of the irrigant bag into the patient through a tube 410. The force of gravity will force the fluid into the patient.

The irrigant fluid flows out of the patient through a tube 412 and enters a collection canister 414. The collection canister is suspended from scale 26 and is preferably large (e.g., 20 liters) so that the collection canister does not have to be changed or emptied often. The collection canister may also have a fitting 416 which allow a suction device (not shown) to be attached to increase fluid flow out of the patient.

While the above is a complete description of the preferred embodiments of the invention, various alternatives, modifications and equivalents may be used. It should be evident that the present invention is equally applicable by making appropriate modifications to the embodiments described above. For example, the weighing devices in a preferred embodiment are scales including load cells but other weighing devices may be utilized (e.g., compression scales). Therefore, the above description should not be taken as limiting the scope of the invention which is defined by the metes and bounds of the appended claims.

What is claimed is:

1. A device for measuring fluid retention or loss of a patient, comprising:

a first weighing device that weighs fluid in an inflow container to produce a fluid-in weight, the inflow container supplying fluid introduced into the patient;

a second weighing device that weighs fluid in an outflow container to produce a fluid-out weight, the outflow container collecting fluid from the patient;

a processor, coupled to the first and second weighing devices, that calculates fluid retention or loss of the patient according to the fluid-in and fluid-out weights, the processor automatically detecting if an inflow or outflow container is replaced; and a display device, coupled to the processor, that displays the fluid retention or loss of the patient.

2. The device of claim 1, wherein the processor automatically detects if a weight of an inflow or outflow container is zero, indicating that the inflow or outflow container has been removed.

3. The device of claim 2, wherein the processor signals a user when the inflow or outflow container has been removed.

4. The device of claim 1, wherein the processor automatically detects if a weight of an inflow or outflow container increases after being zero, indicating that the inflow or outflow container has been replaced.

5. The device of claim 4, wherein the processor signals a user when the inflow or outflow container has been replaced.

6. The device of claim 1, wherein the processor resets a baseline weight of the replaced container.

* * * * *

UNITED STATES PATENT AND TRADEMARK OFFICE
CERTIFICATE OF CORRECTION

PATENT NO. : 6,319,221 B1
DATED : November 20, 2001
INVENTOR(S) : Savage et al.

It is certified that error appears in the above-identified patent and that said Letters Patent is hereby corrected as shown below:

<u>Column 1</u>,
Line 4, replace the first paragraph with:
-- CROSS REFERENCE TO RELATED APPLICATIONS This application is a divisional application of US serial number 09/068,059, filed on December 14, 1998, now US 6,238,366, which is the national filing of international application PCT/US96/17396, filed on October 31, 1996, which claims priority of US application number 08/548,315, filed on November 1, 1995, now abandoned, and US provisional application 60/006,408, filed on November 9, 1995, now abandoned. --

Signed and Sealed this

Twenty-eighth Day of December, 2004

JON W. DUDAS
*Director of the United States Patent and Trademark Office*